United States Patent
Dayan et al.

(10) Patent No.: US 6,526,828 B1
(45) Date of Patent: Mar. 4, 2003

(54) SENSITIVE AND SELECTIVE METHOD AND DEVICE FOR THE DETECTION OF TRACE AMOUNTS OF A SUBSTANCE

(75) Inventors: Lev Dayan, Holon (IL); Yohai Y. Dayagi, Rehovot (IL); Moshe Shalom, Herzeliya (IL)

(73) Assignee: M.S. Tech Ltd., Nes-Ziona (IL)

( * ) Notice: Subject to any disclaimer, the term of this patent is extended or adjusted under 35 U.S.C. 154(b) by 0 days.

(21) Appl. No.: 09/885,909

(22) Filed: Jun. 20, 2001

(51) Int. Cl.$^7$ ............................................... G01N 29/04
(52) U.S. Cl. .................. 73/579; 73/24.01; 73/54.01; 73/590
(58) Field of Search ................. 73/579, 24.01, 73/54.01, 590, 54.41

(56) References Cited

U.S. PATENT DOCUMENTS

| | | | |
|---|---|---|---|
| 3,164,004 A | | 1/1965 | King, Jr. ..................... 73/24.06 |
| 5,130,257 A | * | 7/1992 | Baer et al. .................. 436/151 |
| 5,177,994 A | | 1/1993 | Moriizumi et al. ......... 73/23.34 |
| 5,201,215 A | * | 4/1993 | Granstaff et al. .......... 73/54.41 |
| 5,283,037 A | * | 2/1994 | Baer et al. ................. 422/68.1 |
| 5,705,399 A | * | 1/1998 | Larue ........................ 73/61.75 |
| 5,817,921 A | | 10/1998 | Tom et al. ................. 73/24.01 |
| 5,852,229 A | * | 12/1998 | Josse et al. ............... 73/24.06 |
| 6,085,576 A | | 7/2000 | Sunshine et al. .......... 73/29.01 |
| 6,111,341 A | * | 8/2000 | Hirama ...................... 310/365 |
| 6,290,839 B1 | * | 9/2001 | Kayyem et al. ......... 205/777.5 |

FOREIGN PATENT DOCUMENTS

| | | |
|---|---|---|
| EP | 992768 | 4/2000 |
| JP | 1244335 | 9/1989 |
| JP | 5187986 | 7/1993 |

OTHER PUBLICATIONS

Fatibello–Filho, O., Suleiman, A.A., & Gullbaulh, G.G. (1991). Piezoelectric Crystal Sensor for the Determination of Formaldehyde in Air. *Talanta,* vol. 38, No. 5, pp. 541–545.

Moriizumi, T., & Nakamoto, T. (Nov. 9–13, 1992). Odor Sensing Systme Using Neural Network Pattern Recognition. *Signal Porocessing and Systems Control Intelligent Sensors and Instrumentation: International Conference on Industrial Electronics, Control, Instrumentaion, and Automation.* vol. 3 of 3, pp. 1645–1649. San Diego, U.S.A.

Moy , L., & Collins, M. (Feb., 1996). Electronic Nose and Artificial Neural Networks. *American Chemical Society,* Anal. Chem., 58, pp. 3077–3084.

* cited by examiner

*Primary Examiner*—Hezron Williams
*Assistant Examiner*—Jacques Saint-Surin
(74) *Attorney, Agent, or Firm*—Greer, Burns & Crain, Ltd.

(57) ABSTRACT

A piezoelectric crystal element and a sensor utilizing the same are presented for use in a sensor device for identifying at least one foreign material from environment. The crystal element comprises at least one crystal resonator in the form of an inverted mesa structure, which has a membrane-like region and is characterized by a certain resonance frequency value. A surface region of the crystal resonator is modified by reactive molecules of a kind capable of interacting with the foreign material to yield a reaction product that effects a change in the resonance frequency of the crystal resonator from said certain resonance frequency value. This change is indicative of the identity and quantity of the foreign material.

30 Claims, 4 Drawing Sheets

SENSITIVE AND SELECTIVE METHOD AND DEVICE FOR THE DETECTION OF TRACE AMOUNTS OF A SUBSTANCE

FIELD OF THE INVENTION

This invention is in the field of mass detection using a coated piezoelectric sensor.

BACKGROUND OF THE INVENTION

In recent years there has been a growing interest in coated piezoelectric crystals, not only as highly sensitive and selective detector of various air pollutants but also as simple, inexpensive and portable device. The high sensitivity and simple relationship between mass and frequency make the quartz crystal microbalance as an ideal tool for the study of adsorption, and as a selective chemical sensor in many applications.

The principle of the detection is that the frequency of vibration of an oscillating crystal is decreased by the adsorption of a foreign material on its surface. A gaseous pollutant is selectively adsorbed by a coating on the crystal surface, thereby increasing the weight of the crystal and decreasing the frequency of vibration. The decrease in the frequency is proportional to the increase in weight due to the presence of gas adsorbed on the coating according to the following equation: $\Delta F = K \cdot \Delta C$. Here, $\Delta F$ is the frequency change (Hz), K is a constant which refers to the basic frequency of the quartz plate, area coated, and a factor to convert the weight of injected gas (g) into concentration (ppm), and $\Delta C$ is concentration (ppm) of sample gas.

U.S. Pat. No. 3,164,004 teaches that a piezoelectric quartz crystal coated with a substrate selectively sensitive to changes in the atmospheric environment can serve as a detection device in fluid analyzers. In general, this discovery is based on the principle that the oscillation of a crystal, both in frequency and amplitude, is in part a function of its weight. The change in weight of a crystal coated with a substrate selectively sensitive to a particular contaminant when placed in an environment containing that contaminant is, in turn, at least partly a function of the concentration of the contaminant. Therefore, the measurement of the change in oscillation characteristics of a coated crystal sensitive to a particular contaminant upon exposure to a given atmosphere is a direct and highly sensitive measure of the presence and concentration of that contaminant. Variations of and improvements in this basic method are shown, inter alia, in the following publications U.S. Pat. Nos. 5,177,994; 5,817,921, and 6,085,576; Japanese Patents Nos. 1244335, and 5187986; European Patent No. 992768, and "*Electronic Nose and Artificial neural Networks*", L. Moy and M. Collins, American Chemical Society, Anal. Chem., 1986, 58, pp. 3077–3084; "*Piezoelectric Crystal Sensor for the Determination of Formaldehyde in Air*", Talanta, Vol. 38, No. 5, pp. 541–545, 1991; "*Odor Sensing System Using Neural Network Pattern Recognition*", Toyosaka Moriizumi and Takamichi Nakamoto, International Conference on Industrial Electronics, Control, Instrumentation and Automation, Nov. 9–13, 1992, Marriot Mission Valley, San Diego, USA.

A sensor has two equally important requirements: sensitivity and selectivity. There are two ways of achieving high selectivity and specificity towards xenobiotic (non-self) agents as we can learn from nature: (i) the immune system, in which a unique sensor (i.e. antibody) is being synthesized for any invader (i.e. antigen). This is a very complicated mechanism that involves a spontaneous constant synthesis of new molecules that are examined to fit the antigen; (ii) the olfactory system, in which a huge array of receptors are located in the nose in such a way that a molecule entering the nose interacts with some of the receptors; the brain then translates the pattern of the signals to an odor. In this case the odor can be a single molecule or a composition of several different molecules.

The combination of a number of sensors and a pattern recognition routine is known as an "electronic nose". Using the combination of chemical sensors, which produce a fingerprint of the vapor or gas, the recognition algorithms can identify and/or quantify the analytes of interest. The electronic nose is capable of recognizing unknown chemical analytes, odors, and vapors. In practice, an electronic nose is presented with a substance such as an odor or vapor, and the sensor converts the input of the substance into a response, such as an electrical response. The response is then compared to known responses that have been stored previously. By comparing the unique chemical signature of an unknown substance to "signatures" of known substances, the unknown analyte can be determined. A variety of sensors can be used in electronic noses that respond to various classes of gases and odors.

A wide variety of commercial applications are available for electronic noses including, but not limited to, detection of explosives or drugs, environmental toxicology, biomedicine, such as microorganism classification or detection, material quality control, food and agricultural product monitoring, ambient air monitoring, employee protection, emissions control, and product quality testing. Referring to the detection of explosives, a number of laboratory techniques for the detection of explosives are known, using gas chromatography, mass spectrometry, ion mobility spectroscopy, NMR, plasma chromatography and visible chromatography. While some of these techniques are capable of ppb detection, the detection systems need elaborate techniques for operation, are usually not portable and simple, and are thus not useful for field use.

SUMMARY OF THE INVENTION

The electronic noses of today are not sensitive enough and are not very versatile, and may in some instances require a very large number of sensors and data power, making them rather expensive and slow.

Thus, there is still a need in the art for a sensing device that is compact, capable of detecting trace amounts of mass of $10^{-15}$ g order and even less, that is useful in a broad variety of applications and can respond accurately to a broad variety of gases, analytes, odors and fluids.

The present invention provides a sensing device (also referred to as an electronic-nose device) that is compact and, in certain embodiments, configured to be a handheld device. The device can be used to measure or identify one or more analytes in a medium such as vapor, liquid or gas.

The main idea of the present invention is based on the use of a piezoelectric crystal element (such as quartz, ceramics), which, on the one hand, can be manufactured by the existing techniques to be mountable in a sensor device, and, on the other hand, has a sufficiently thin (membrane-like) region, which defines a sensing region, thereby providing increased sensitivity as compared to the known sensors.

It is known that the less the thickness of a piezoelectric quartz crystal, the higher the sensitivity of the sensor device. The crystal element, according to the present invention, is in the form of the so-called "inverted mesa structure", in which a relatively thin membrane-like region (resonator) is surrounded by relatively thick end regions of the structure. This membrane-like region is provided with a pair of electrodes. The electrodes and/or the membrane-like region have a surface region coated with reactive molecules, thereby presenting a sensing region of the device electrically excitable by the environment (which can be gas or liquid). The reactive coating molecules interact with a foreign material from the environment to yield a reaction product that effects a change in the resonance frequency of the crystal resonator from a certain resonance frequency value characterizing said crystal resonator.

The reactive coating molecules are preferably organized in a self-assembled monolayer (SAM) formed on the surface of the electrodes and/or the membrane-like region (i.e. on the surface of a substrate). The monolayer consists of receptor compounds comprising a linker that connects said compound to the surface of said substrate, an optional spacer, a structural element and an active head group.

There is thus provided according to one aspect of the present invention, a piezoelectric crystal element for use in a sensor device for identifying at least one foreign material from environment, the crystal element comprising at least one crystal resonator in the form of an inverted mesa structure having a membrane-like region and being characterized by a certain resonance frequency value, a surface region of said at least one crystal resonator being modified by reactive molecules of a kind capable of interacting with said at least one foreign material to yield a reaction product that effects a change in the resonance frequency of said crystal resonator from said certain resonance frequency value, said change being indicative of the identity and quantity of said at least one foreign material.

According to another aspect of the present invention, there is provided a piezoelectric sensor for use in a device for identifying at least one foreign material from environment, the sensor comprising a piezoelectric crystal element having at least one crystal resonator in the form of an inverted mesa structure defining a sensing membrane-like region and being characterized by a certain resonance frequency value, and electrodes formed on opposite sides of said sensing membrane-like region, said at least one crystal resonator having a surface region modified with molecules capable of interacting with at least one foreign material from the environment to which the crystal resonator is exposed to yield a reaction product that effects a change in the resonance frequency of said at least one crystal resonator from said certain resonance frequency value, said change being indicative of the identity and quantity of said foreign material.

The input and output of the sensor is connectable to a control means operable for actuating the at least one crystal resonator and measuring the change in the resonance frequency, to generate measured data representative of the identity and quantity of said foreign material.

The metal electrodes used in the sensor may comprise a metal selected from Au, Pt and Al, with Au being the most preferred metal. The modified surface region may include the surface of the membrane region, the surface of the respective electrode, or both.

The control means comprises an actuator utility (oscillator and one or more switches depending on the number of crystal resonators) and a detector utility. The actuator utility actuates said at least one crystal resonator to put it in operation. The detector utility comprises an electronic circuit for detecting the frequency of the at least one crystal resonator to enable measurement of said change.

According to yet another aspect of the present invention, there is provided a piezoelectric sensor device for identifying at least one foreign material from environment, the device comprising:

(i) a sensor including a piezoelectric crystal element having at least one piezoelectric crystal resonator in the form of an inverted mesa structure defining a sensing membrane-like region and being characterized by a certain resonance frequency value, and electrodes formed on opposite sides of said sensing membrane-like region, said at least one crystal resonator having a surface region modified with molecules capable of interacting with a foreign material of the environment to yield a reaction product that effects a change in the resonance frequency of said at least one crystal resonator from said certain resonance frequency value, said change being indicative of the identity and quantity of said foreign material; and (ii) a control means operable for actuating said at least one crystal resonator, measuring the change in the resonance frequency of said at least one crystal resonator, and generating measured data representative of the identity and quantity of said foreign material.

Preferably, the crystal element comprises an array of spaced-apart crystal resonators, each in the form of the inverted mesa structure formed with a pair of electrodes at opposite surfaces of the membrane-like region, thereby defining an array of sensing regions affectable by the environment. The surface regions of different crystal resonators are modified with different reactive molecules, thereby enabling the detection of various foreign materials contained in the environment. Au electrodes, for example, are suitable for modification with sulfur containing molecules. When the quartz membrane region participates in the sensing operation, then the quartz may be modified by different functional groups, such as, for example, silanes.

The crystal element may comprise the so-called "reference" or "passive" crystal resonator (without coating) which is screened from the environment. The change of the resonance frequency of the "active" crystal resonator caused by the foreign material is thus determined as a difference between the resonance frequencies of the active and passive elements. Alternatively, such reference data (or the certain value of the resonance frequency characterizing the crystal resonator) may be stored in a memory of the control means.

Preferably, the crystal resonators are equally distanced from the actuator utility. This may be implemented by arranging the resonators (wherein one of the crystal resonators may be the reference or passive element) in spaced-apart relationship along a circular path and placing the actuator utility either in the center of the circle or at any other location at the central axis of the circle. Thus, the crystal element may comprise a disc carrying the circular array of the equally spaced piezoelectric crystal resonators, and the actuator utility located on the central axis of the disc. It should be understood that the entire disc may be made of a piezoelectric crystal, in which case the crystal is patterned to define the circular array of spaced-apart inverted mesa structures (i.e., the circular army of membrane-like regions defining the sensing regions). Alternatively, such inverted mesa structures of piezoelectric crystal resonators may be mounted on a disc made of any other suitable material.

According to yet another aspect of the present invention, there is provided a piezoelectric sensor device for identifying at least one foreign material from environment the sensor device comprising:

an array of spaced-apart crystal resonators, each crystal resonator being in the form of an inverted mesa structure having a membrane-like region and being characterized by a certain resonance frequency value, each of the crystal resonators being excitable by the environment to cause a change in the resonance frequency thereof from said certain resonance frequency value; and an actuator utility for operating the crystal resonators, said actuator utility being equally spaced from each of the crystal resonators.

The modification of the surface region of the crystal resonator may be achieved by two alternative techniques: (1) construction of organized, self assembled monolayers (SAM); or (2) formation of polymeric layer.

The organized, self-assembled monolayer (SAM) consists of receptor compounds comprising a linker that connects said compound to the surface of said substrate, an optional spacer, a structural element and an active head group.

Relating to the formation of a polymeric layer, the preferred technology for forming a polymer layer in a controlled manner is by electropolymerization It should be noted that the device of the present invention could be used in gaseous medium, liquid medium or a combination thereof, thus acting as an electronic nose and/or as an electronic tongue. An electronic tongue is a device similar to the electronic nose, but capable of operating in a liquid medium, and enables the analysis of solutes in a solution. Such a combined device provides for simultaneous analysis of a solution and it's vapors, providing a complete picture of the detected material.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
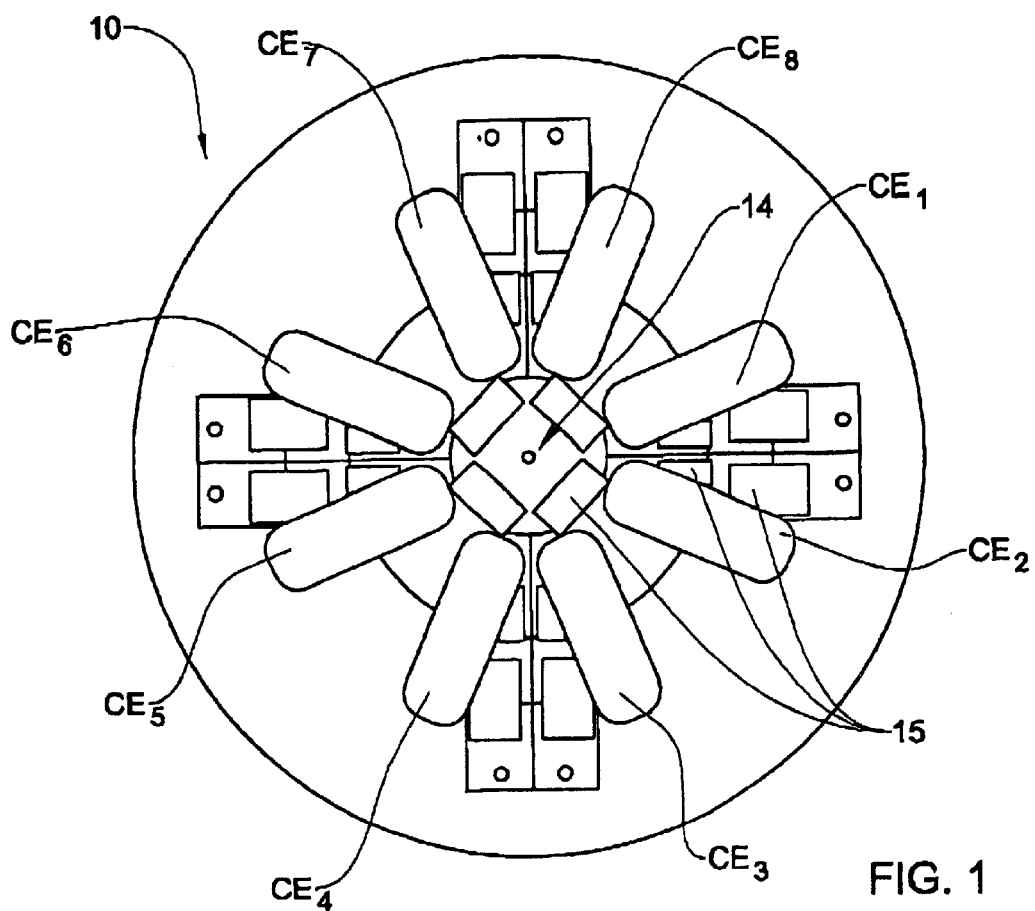
FIG. 1 is a schematic illustration of a sensor device according to the invention.

Referring to FIG. 1, there is illustrated a sensor device 10 according to the invention, which, in the present example, is implemented as a disc-shaped printed circuit board 12. The device 10 comprises such main constructional parts as sensor comprising a piezoelectic crystal element (quartz crystal in the present example), and a control means.

The crystal element may comprise one or more crystal resonators, eight such is resonators $CE_1$–$CE_8$ made of quartz crystal being shown in the present example. The control means comprises electronic components, which are incorporated in the disc 12 and include an actuator utility 14, and a detector utility, generally at 15. The actuator utility is composed of an oscillator, and a plurality of switches associated with the crystal resonators, respectively, as will be described more specifically further below with reference to FIG. 4.

The quartz crystal resonators $CE_1$–$CE_8$ are arranged in a spaced-apart relationship along a circular path centered around the actuator utility 14. This arrangement equally distances all the quartz crystal resonators from the oscillator utility 14. It should be understood that the same can be achieved by placing the oscillator utility at any location on the central axis of the circle formed by the array of equally spaced quartz crystal resonators.

It should be noted, although not specifically shown, that one of the crystal resonators may be a reference one screened from the environment to which the other "active" resonators are exposed. The provision of such a reference crystal resonator is optional, and may be replaced by the storage of a reference signal in a memory of the control means.

Figure 2A:
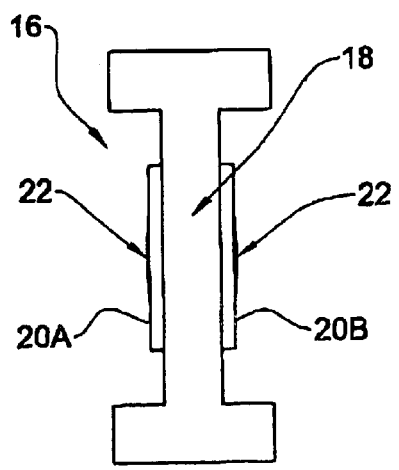
FIGS. 2A and 2B more specifically illustrate a crystal resonator in a piezoelectric crystal element of the device of FIG. 1.
Figure 2B:
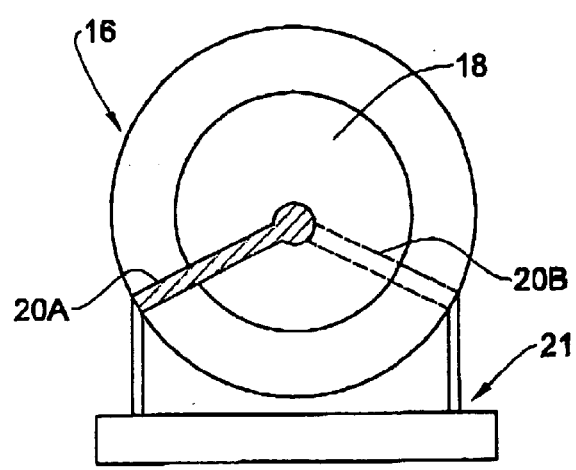

Turing now to FIGS. 2A and 2B, each of the quartz crystal resonators is an inverted mesa structure 16 defining a membrane-like region 18 having a thickness of about several micrometers. To fabricate such an inverted mesa structure, a crystal is patterned either at one side thereof to form one recess, or at both opposite sides thereof to form two opposite recesses, thereby forming the membrane central region 18 of a sufficiently small thickness (to obtain desirably high sensitivity of the sensor device) between two relatively thicker end portions of the structure. Metal electrodes 20A and 20B (made fxom Al, Pt or Au) are deposited onto opposite surfaces of the membrane-like region 18. As shown in the example of FIG. 2B (illustrating a crystal element with a single resonator), the crystal element is supported by a holder 21. Preferably, Au-based glue is used for attaching the crystal element to the holder.

The active quartz crystal resonator is formed with a surface region 22 (exposed to the environment) modified by reacting molecules intended to interact with one or more specific foreign materials that may be present in the environment. In the present example, this is implemented by coating the electrodes 20A, and 20B with such a molecule, as will be described more specifically further below. It should, however, be noted that, generally, such a modified surface region may include the surface of the electrodes (or only one electrode located on that side of the device by which it is exposed to environment), the surface of the membrane-like region, or both. An interaction between these molecules and one or more specific foreign material affects the frequency of vibration of the crystal resonator to change from the certain resonance frequency value. This change is detected by the corresponding electronic component of the control means.

As indicated above, the principle of the detection is that the frequency of vibration of an oscillating crystal is decreased by the absorption of a foreign material on its surface. A foreign material, for example a gaseous pollutant, is selectively absorbed by the coating (on the crystal surface or/and on the metal electrode surface coating the crystal surface), thereby increasing the weight of the crystal and decreasing the frequency of vibration. The decrease in the frequency $\Delta F$ (Hz) of the crystal resonator is proportional to the increase in its weight due to the presence of foreign material absorbed on the coating and is represented by the following equation: $\Delta F = K \cdot m$, where m is the change in mass per unit surface area and K is a constant which refers to the basic frequency of the piezoelectric crystal plate.

Figure 3A:
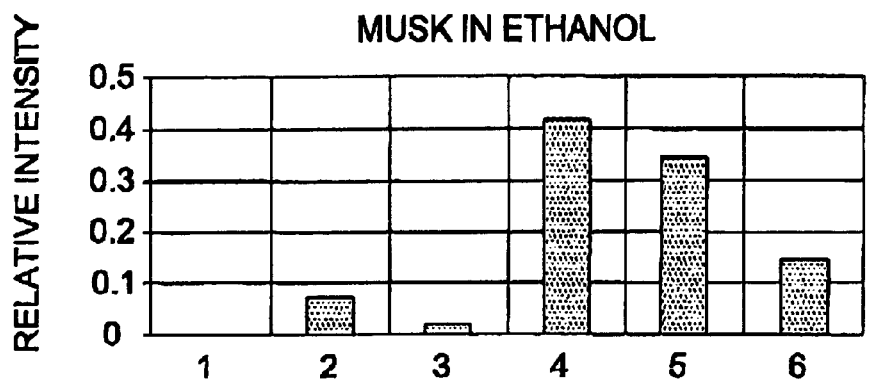
FIGS. 3A to 3C illustrate experimental results of the absorption of three different analytes: musk in ethanol, TATP and TNT.
Figure 3B:
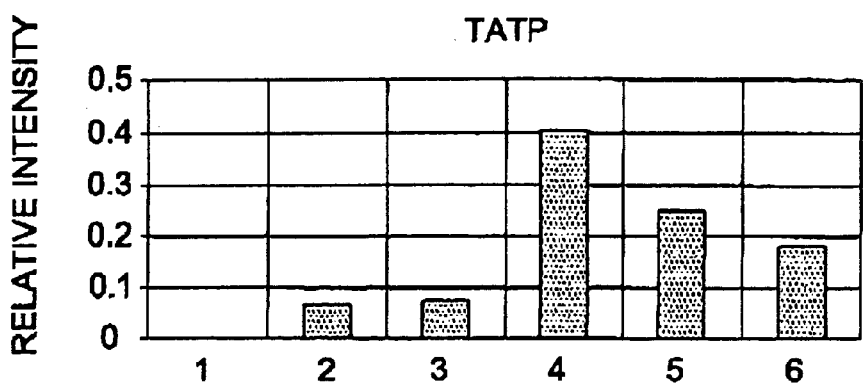
Figure 3C:
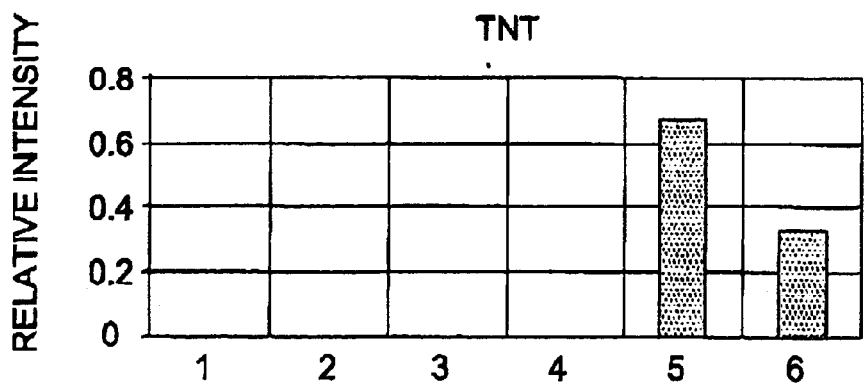

It should be understood that what is actually detected by the device of the present invention utilizing several crystal resonators is the so-called "electronic image" or pattern of the intensities of response of each of the crystal resonators in the crystal element. These responses are indicative of the decay of the vibrating frequencies of the crystal resonators caused by the absorption of foreign materials. FIGS. 3A to 3C illustrate experimental results in the form of three different measured patterns (electronic images), respectively, of the absorption of three different analytes: musk oil in ethanol, TATP and TNT.

Figure 4:
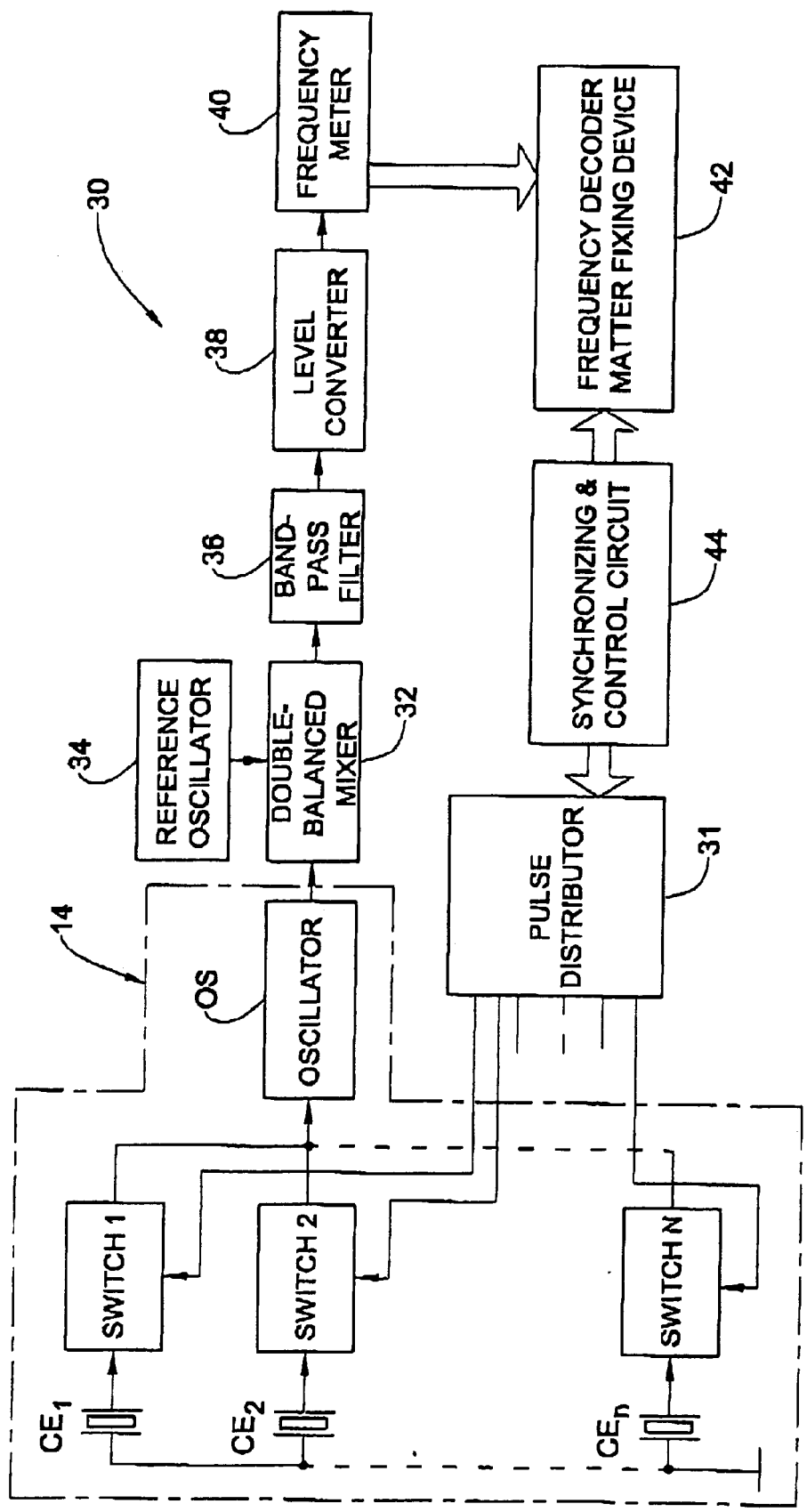
FIG. 4 is a block diagram of the device of FIG. 1 showing more specifically a control means of the device.

FIG. 4 illustrates a block diagram of the sensor device 10, showing the main components of the control means 30 for operating and processing the response of (n−1) active quartz crystal resonators $CE_2$–$CE_n$ utilizing a reference (passive) quartz crystal resonator $CE_1$. The actuator utility 14 of the control means 30 comprises n switches, which, by n input ports thereof are connected to the n quartz crystal resonators $CE_1$–$CE_n$, respectively, and by the output ports thereof, are connected to the input port of an oscillator OS. The switches, by other input ports thereof, are connected to a pulse distributor 31. The oscillator's output is connected to one input port of a double balanced mixer 32, the other input port of the mixer 32 being connected to the output port of a reference oscillator 34. The output port of the double balanced mixer 32 is connected to the input of a band-pass filter 36, whose output port is connected to the input of a level converter 38, which, in turn, is connected by its output port to the input of a frequency meter 40. All the outputs of the frequency meter 40 are connected to the respective inputs of a frequency decoder matter fixing device 42. The other input ports of the device 42 are connected to corresponding output ports of a synchronizing and control circuit 44, whose output ports are connected to the inputs of the distributor 31.

The operation of the device 10 is based on the creation of an electronic image of a certain foreign material and the identification of this material by means of neural network algorithms utilizing an image processing (pattern recognition) technique. The electronic image of a foreign material is created by measuring and analyzing the relative change of frequency of each quartz crystal resonator during the period of creation of the electronic image, as a combination of data generated by all quartz crystal resonators. The relative frequency change of each quartz crystal resonator corresponds to the changes of various conditions affecting the resonator. As described above, the frequency of the quartz crystal resonator is affected by the presence of a foreign material, as well as by changes in the environmental parameters. In order to reduce the effects of the environmental parameters up to a minimal value, the reference resonator $CE_1$, which is insensitive to the foreign material, is used.

The time period of the electronic image creation is defined by the synchronizing and control circuit 44. The electronic image is composed of a preset number of information packages, each package including a given number of measurement cycles. Each cycle is defined by the pulse distributor 31, by means of sequential connection of the resonators $CE_1$–$CE_n$ to the oscillator OS through the respective switches.

When the quartz crystal resonator is connected to the oscillator OS, the latter is excited at the resonance frequency of the resonator, and the oscillator generates a corresponding signal. This signal inputs the double balanced mixer 32, which also receives a reference signal from the reference oscillator 34. The use of the mixer 32 enables to extract a signal of the relative frequency change, while keeping the parameters and the frequency changes profile unchanged, thereby enabling to reduce the measurement time and increase the accuracy of the sensor device. The band-pass filter 36 reduces the level of effects caused by the conversion up to a required value. An output signal of the filter 36 is supplied to frequency meter 40 through the level converter 38. The circuit 40 carried out frequency measurement, and a signal representative of a measured frequency value, simultaneously with information about the number of the respective quartz crystal resonator, cycle and package for the data formation supplied from the synchronizing and control circuit 44, enter the device 42. When the time of the electronic image formation expires, the information packages are mathematically processed, the foreign material is identified and an output signal indicative thereof is generated, being appropriately formatted in accordance with the user requirements.

The following table presents experimental results showing the gas sensor sensitivity of various crystal resonators characterized by different quartz crystal frequencies due to different values of the membrane thickness.

| Frequency (MHz) | 9 | 30 | 150 | 300 |
|---|---|---|---|---|
| Membrane Thickness ($\mu$m) | 185 | 56 | 11 | 5.6 |
| Sensitivity (g) | $1 \times 10^{-9}$ | $9.7 \times 10^{-11}$ | $1.5 \times 10^{-13}$ | $2.4 \times 10^{-15}$ |

It should be understood that by further reducing the membrane thickness, the frequency of the crystal resonators, and, consequently, the sensitivity of the device can be even more increased. For example, with the membrane thickness of 3.3 $\mu$m, the frequency of 500 MHz and sensitivity of $1.7 \times 10^{-15}$ can be obtained.

The modification of the metal surface of the electrode may be achieved by two alternative techniques: (1) construction of organize, self assembled monolayers (SAM); or (2) formation of polymeric layer. These techniques are described hereinbelow:

(1) Construction of Organized SAM

The use of a piezoelectric substance such as quartz crystals covered at least partially with a metallic electrode (either gold, platinum or aluminum) provides an essential tool for the construction of organized organic monolayers. This is so because the presence of an organized metallic layer that chemically differs from its surrounding enables the selective modification of that part with a suitable functional group. A gold or platinum electrode, for example, can be modified by sulfur containing molecules such as thiols, cyclic disulfides or thioethers. Aluminum electrodes can be modified by acidic moieties such as carboxylic acids and sulfonic acids.

Figure 5:
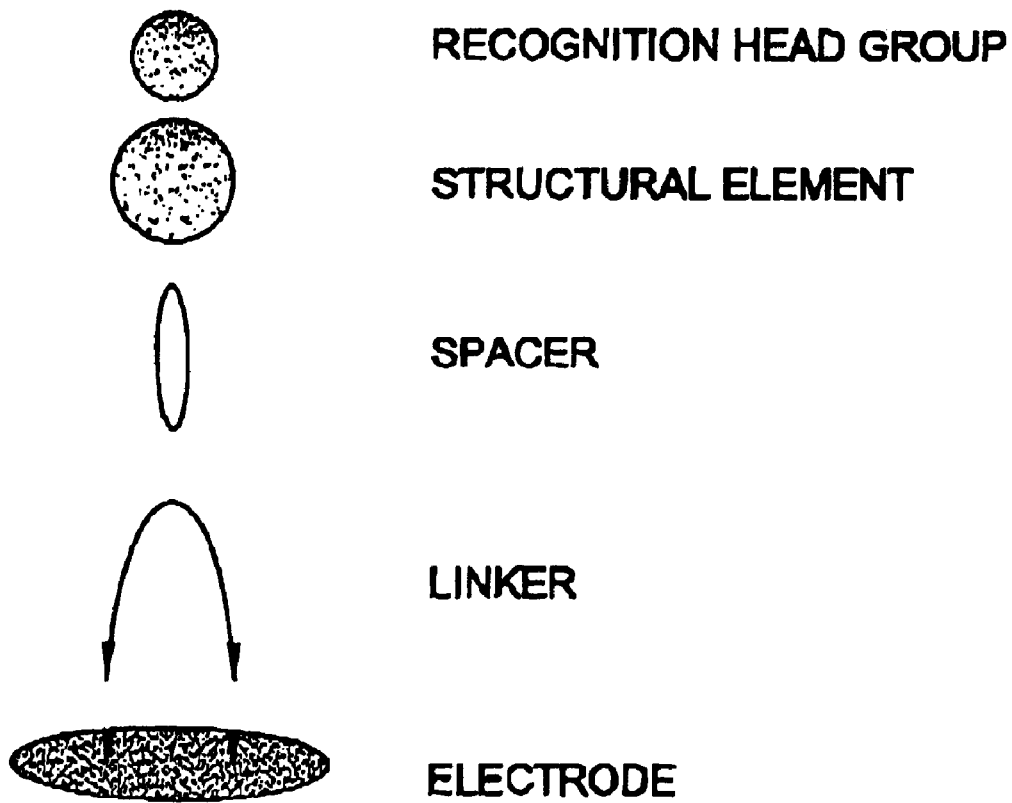
FIG. 5 schematically demonstrates the principles of modification of the metal surface of an electrode in the crystal resonator of FIGS. 2A and 2B by utilizing the construction of organized, self-assembled monolayers (SAM).

The concept of SAM allows us to prepare tailor made organic molecules designed to act as artificial receptors, each binding selectively to an analyte to be detected. Such molecules comprise a linker that connects the entire molecule to the surface of the electrode and/or of the crystal resonator, an optional spacer, a structural element (the structural element and the optional spacer determine the structure and length of the whole monolayer) and an active head group. This is schematically demonstrated in FIG. 5 for a selective receptor molecule prepared on the surface of an electrode.

Such a modular design is the basis for an unlimited arsenal of surface modifications.

The linker is the element that connects the selective receptor molecule to the surface of the electrode and/or the resonator and controls the coverage and smoothness of the monolayer. When the quartz resonators are used with a gold electrode, the linker is based on sulfur-containing compounds, for example thioethers, cyclic disulfides or thiols. Examples of sulfur-containing linker moieties are shown below:

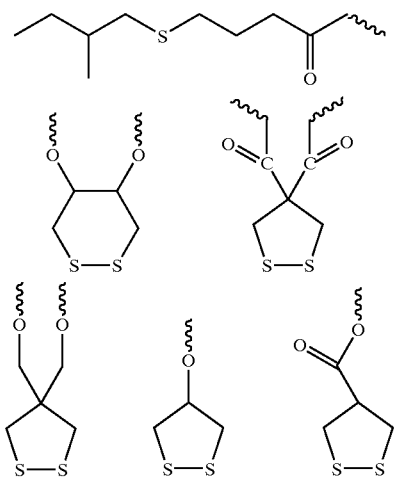

When a spacer is included in the receptor molecules, it may fulfil one or more of the following roles:
(i) To solve synthetic problems of connecting moieties that do not fit by means of functional groups. This is done by using bifunctional spacers such as bromo-acids, diamines etc.
(ii) To control the flexibility of the molecule.
(iii) To introduce some chiral discrimination when a chiral spacer is used.

The structural elements are based on molecules which promote the strong packing of the layers. Examples of such molecules are aromatic molecules, e.g. phenyl naphthyl or larger rings, that may be optionally substituted by at least one substituent or amino acids optionally substituted that might stabilize the monolayer through hydrogen bonds. The substituents may be of various structures, e.g. electron withdrawing or electron donating groups, depending on the characteristics of the foreign substance to be detected.

The bead groups may interact with a specific foreign substance by various mechanisms, for example by foaming a chemical bond or by creating a transition state resulting from weak interactions between compatible moieties, depending on the characteristics of the substance and the head group. Examples of head groups are amino, nitro, hydroxyl, thio, thiol, carboxyl and carboxyl derivatives.

Examples of chemical reactions are between functional groups such as carbazido groups and ketones to form Schiff bases (imines) or between boronic acids and diols to form boronic esters.

Except for the functional groups, the head group may also bear various substituents that affect the electron density of this element, thus altering the strength of the chemical bond or interaction between the monolayer and the substance to be detected.

The following artificial receptors with varying substituents on the head group have been prepared.

Formula

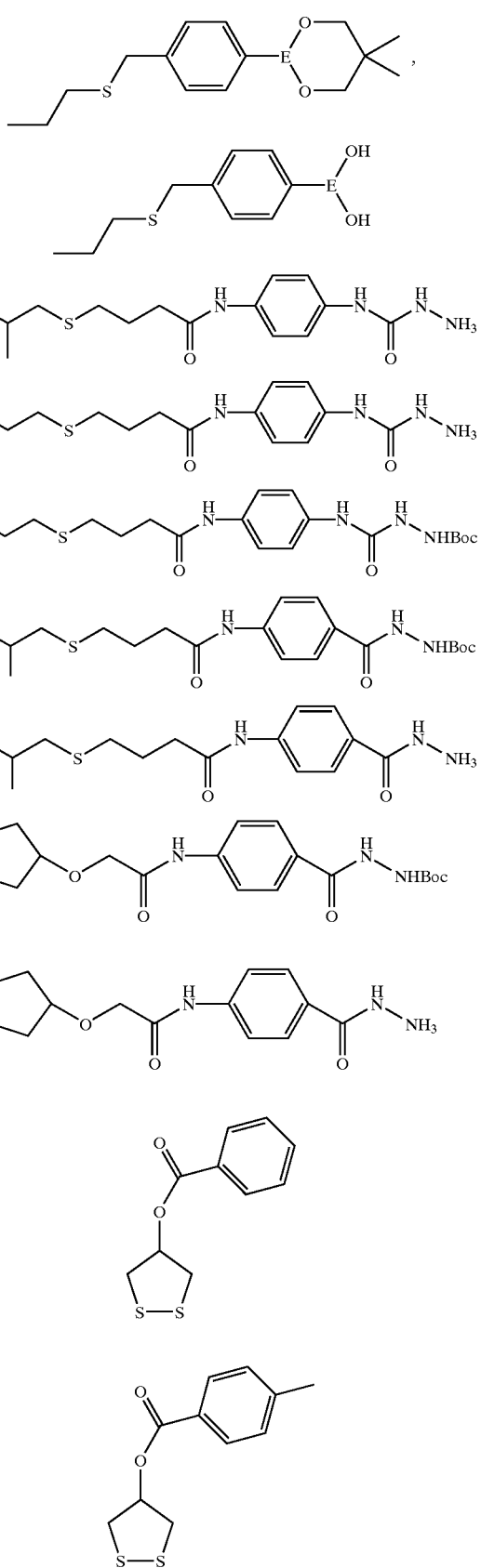

-continued

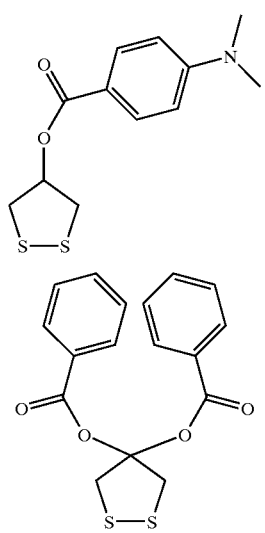

The above compounds are novel and constitute a further aspect of the invention.

(2) Formation of Polymeric Layer

As already mentioned above, the modification of the metallic surface of the electrode can be achieved by two alternative ways, by SAM formation or by polymeric layer formation. Relating to the formation of a polymeric layer, the preferred technology for forming a polymer layer on a metallic surface in a controlled manner is by electropolymerization.

The following polymeric layers were produced and examined for adsorbing explosives: polypyrrole, polythiopliene, polytriphenylene, poly(dimethylammo)pyrrole, polyaniline, poly(N-phenyl)aniline, poly(N-methyl)aniline and polyfluoroanline.

The electronic nose of the invention has potential use for the detection of hidden explosives. The chemical structures of some important explosives that are widely used by terrorists, including TATP (triacetone triperoxide) are shown hereinbelow:

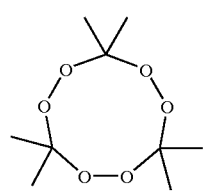

TATP

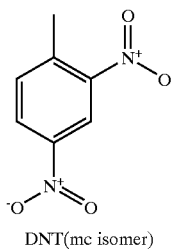

DNT(mc isomer)

-continued

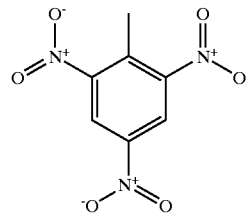

TNT

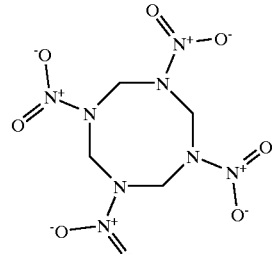

HMX

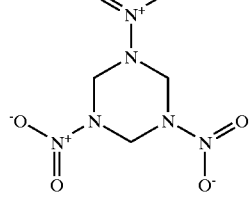

RDX

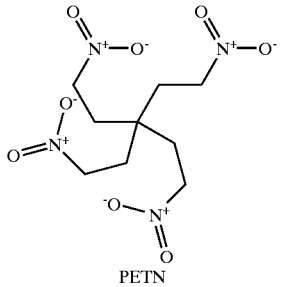

PETN

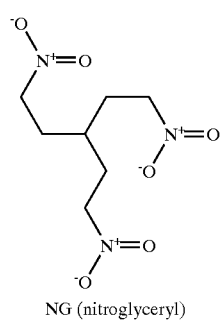

NG (nitroglyceryl)

The present invention is now described by the following non-limiting examples:

EXAMPLES

Example 1

General Procedure for the Preparation of a Monolayer

A quartz crystal resonator provided with a pair of gold electrodes on both surfaces thereof was treated with a solution of an sulfur molecule (0.1 mM in absolute ethanol) for 12 hours at 60° C. The resonator was then soaked for 30 min in ethanol, first at 60° C. and then at 30° C., afterwards in acetone for 20 min. at 30° C. three consequent times and dried at 60° C. for 1 hour. The thickness of the reactive monolayer formed is estimated by the change of the resonator frequency, considering also other parameters such as the electrode diameter and the quartz' density. The practically used equation for 300 MHz resonators is as follows:

$$\Delta h = \frac{-\Delta f}{-2.07 \cdot 10^{11} \rho}$$

where $\Delta h$ is the thickness of coating (Å); $\Delta f$ is the difference in frequency (Hz) (coated vs. uncoated); $\rho$ is the density of coating (g/cm$^3$), and the coefficient ($-2.07.10^{11}$) presents the effect of the electrode diameter and the quartz' density. The value of $\rho$ is estimated to be 1.3 (according to literature).

Example 2
Preparation of Polyaniline on Quartz Resonator

A thin layer of polyaniline on quartz resonator provided with gold electrodes was prepared by two alternative methods:
1. By electropolymerization of an aqueous solution of 0.1M aniline+1M methansulfonic acid, using a potential cycling at 0–0.85V(vs. A/AgCl, KCl sat.) range; followed by rinsing in water and drying at 60° C.
2. By a two steps method: a) pretreatment of the resonator with an ethanolic solution of 0.001M 4-aminothiophenol for 18 hrs. at room temperature; followed by rinsing in ethanol and water, to form on the resonator surface a layer of 4-aminothiophenol;
b) Electropolymerization of the product obtained in step a) in an aqueous solution of 0.1M aniline+1M methansulfonic acid, using a potential cycling at 0–0.85V(vs. Ag/AgCl, KCl sat.) range; followed by rinsing in water and drying at 60° C.

In the second method the polymerization is carried out on a preformed layer of 4-aminothiophenol in order to increase the stability of the formed polymeric layer and its uniformity.

Example 3
Synthesis of O-benzoyl [1,2]dithiolan-4-ol (2)

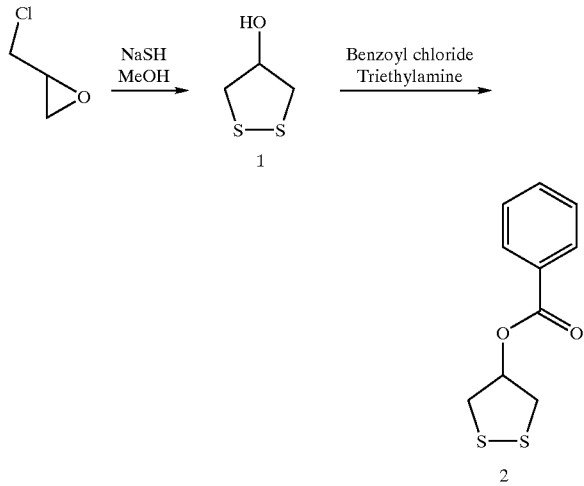

Epichlorohydrin (3 ml, 0.029 mol) was added to a solution of NaSH (1.5 g, 0.27 mol) in MeOH (115 ml). The solution was stirred at room temperature over night. MeOH was evaporated, the residue was dissolved in brine (i.e. saturated aqueous NaCl solution), extracted several times with chloroform, dried with sodium sulfate, filtered and evaporated to dryness. The product was not purified for further reaction.

Benzoyl chloride (1.4 ml) and triethyl amine (1.2 ml) were added to a solution of [1,2]Dithiolan-4-ol (1) (1 g. not pure) in dry dichloromethane (30 ml). The solution was stirred at room temperature under nitrogen over night. Dichloromethane was added to the solution, extracted several time with aqueous $K_2CO_3$ 5%, HCl 1N and Brine, dried over sodium sulfate, filtered and evaporated to dryness.

The product obtained was purified by a flash column chromatography of Silica gel with dichloromethane:hexane (2:1) as eluent to give the product (2); NMR (CDCl$_3$, 250 MHz) $\delta$=8.03(m, 2H, Ar$_m$), 7.58(m, 1H, Ar$_p$), 7.43(m, 2H, Ar$_o$), 5.48(m,1H, SCH$_2$CHO), 3.21(m,4H, SCH$_2$CHO); IR (CHCl$_3$) $\nu$=1734 cm$^{-1}$ (ester).

Example 4
Synthesis of the thioether carbazido molecule (7)

Compound 7 is a representative of the molecules that were synthesized for the construction of SAM. It is a thioether formed from butyric acid and methyl butane thiol, conjugated to a carbazide derivative of phenylene diamine. The synthesis includes 5 steps: nucleophilic substitution that forms a thioether group, hydrolysis of the ester protecting group, coupling to phenylene diamine, reaction with butyl carbazate to form a protected carbazide, followed by deprotection and purification.

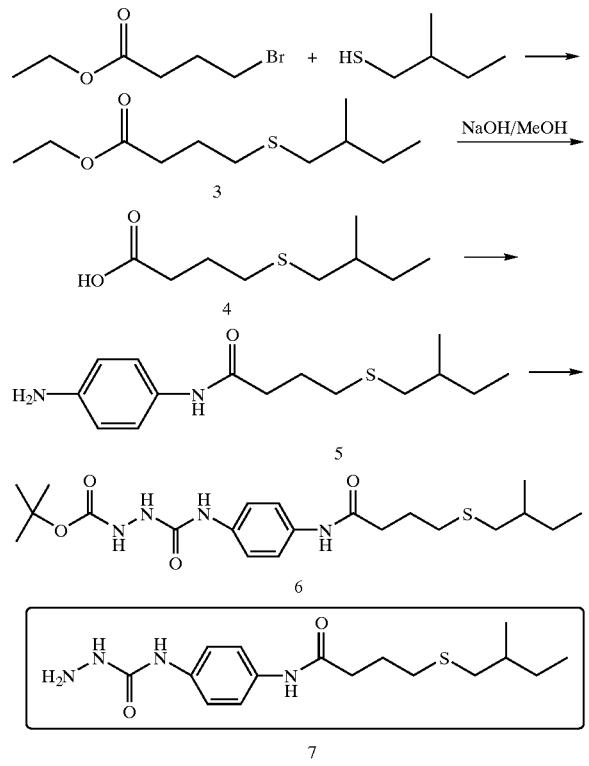

Synthesis of 3:

Anhydrous potassium carbonate was added to a solution of 2-methyl-1-butanethiol in DMF. Bromo ethylbutyrate was added and stirred over night.

The solution was dissolved in a mixture of hexane/ethyl acetate (1:3) and washed several times with water, dried over $Na_2SO_4$, filtered and evaporated to dryness. The product 3 may contain traces of the thiol.

Synthesis of 4:

The ester 3 was dissolved in MeOH (10 ml/mmol) and 1N NaOH (1.1 ml) and stirred for 1 hour. In a case that the reaction was not ended, additional aliquot of NaOH was added. After the consumption of the ester, MeOH was evaporated, the residue was dissolved in water and washed with EtOAc. The basic aqueous solution was acidified with $KHSO_4$ 1M to pH 4. The product was extracted seveal times with EtOAc, dried over $Na_2SO_4$, filtered and evaporated to dryness. The overall yield of the two steps is close to quantitative.

NMR ($CDCl_3$, 250 MHz) $\delta=2.5$(m, 6H three methylene groups), 1.85 (m, 2H, $SCH_2CH_2CH_2$), 1.47 (m, 2H, $CH_3CH_2CH(CH_3)$), 1.18 (m, 1H, $CH_3CH_2CH(CH_3)$), 0.94 (d, J=6.5 Hz, 3H, $CH_3CH_2CH(CH_3)$), 0.87(d, J=7Hz, 3 H $CH_3CH_2CH(CH_3)$). IR ($CHCl_3$) $\nu=1715$ $cm^{-1}$ (COOH).

Synthesis of 5:

Oxalyl chloride (4.5 ml) and a few drops of DMF were added to a solution of the acid 4 (1.6 gr.) in dry dichloromethane and kept under inert atmosphere over night. The solvents were removed in vacuo, the residue was dissolved in dry dichloromethane and introduced in a dropping funnel under nitrogen stream. The acyl chloride was added dropwise to a solution of p-phenylene diamine in DMF (3.5 ml in 15 ml DMF) and the mixture was stirred for two hours. Chloroform was added and the organic solution was washed with water and dried. The product was purified by flash column chromatography (chloroform: MeOH 95:5 as eluent) to give 900 mg product. Yield 40%.

NMR ($CDCl_3$, 250 MHz) $\delta=7.5$(b, 1H, CONHAr), 7.25+6.6 (Abq, 4H,Ar) 2.5 (m, 6H, three methylene groups), 1.95 (m, 2H, $SCH_2CH_2CH_2$), 1.5 (m, 2H, $CH_3CH_2CH(CH_3)$), 1.2 (m, 1H, $CH_3CH_2CH(CH_3)$), 0.94 (d, J=6.5 Hz, 3H, $CH_3CH_2CH(CH_3)$), 0.87 (d, J=7 Hz, 3H, $CH_3CH_2CH(CH_3)$). IR ($CHCl_3$) $\nu=1670$ $cm^{-1}$ (CONH).

Synthesis of 6:

Triphosgene (400 mg.) and 2,6 lutidine (1 ml) were added to a solution of the free amine 5 (900 mg) in dry dichloromethane under inert atmosphere and stirred for 10 min. t-Bu-carbazate (500 mg) was added and the mixture was left for an hour. Chloroform was added and the organic solution was washed with $NaHCO_3$ 1N, HCl 1N, water and dried. The product was purified by flash column chromatography (chloroform: MeOH 95:5 as eluent) to give 700 mg almost pure product 6. The product was recrystalized from MeOH/ether to give 500 mg of pure 6. Yield 35%. NMR ($CDCl_3$, 250 MHz) $\delta=8.27$ (b, 1H, NHNHBoc), 7.79 (b, 1H, NHNHBoc), 7.4 (b, 1H, CONHAr), 7.7 (m, 4H,Ar), 2.5 (m, 6H, three methylene groups), 1.98 (m, 2H, $SCH_2CH_2CH_2$), 1.5 (m, 1H, Boc+$CH_3CH_2CH(CH_3)$), 1.2 (m, 1H, $CH_3CH_2CH(CH_3)$), 0.97 (d, J=6.5 Hz, 3H, $CH_3CH_2CH(CH_3)$), 0.88(d, J=7 Hz, 3H, $CH_3CH_2CH(CH_3)$). IR ($CHCl_3$)) $\nu=1670$ $cm^{-1}$ (CONH), 1710 $cm^{-1}$ (Boc).

Synthesis of 7:

The boc protected semicarbazide 6 (160 mg.) prepared above was treated with 15% TFA in dichloromethane over might, the solvent was removed, the residue was treated with triethylamine (in methanol) to obtain neutral pH, dried, and purified by flash column chromatography (chloroform: MEOH 95:5 as eluent) to give 100 mg of product 7. Yield 80%.

NMR (MeOD+$CDCl_3$, 250 MHz) $\delta=7.4$ (m, 4H,Ar), 2.45 (m, 6H, three methylene groups), 1.92 (m, 2H, $SCH_2CH_2CH_2$), 1.4 (m, 2H, $CH_3CH_2CH(CH_3)$), 1.1 (m, 1H, $CH_3CH_2CH(CH_3)$), 0.89 (d, J=6.5 Hz, 3H , $CH_3CH_2CH(CH_3)$), 0.83 (d, J=7 Hz, 3H, $CH_3CH_2CH(CH_3)$).

Example 5

The frequency change due to exposing several resonators to the vapors (saturated atmosphere according to vapor pressure) of three explosive materials: TATP, TNT and RDX is showed in the following table:

| Coating | TATP | TNT | RDX |
|---|---|---|---|
| Poly(N-methylaniline) | 2350 Hz | 290 Hz | |
| Polytriphenylene | 195 Hz | | |
| Polyaniline | 6000 Hz | | 90 Hz |
| Poly(phenylthiophene) | | | 179 Hz |
| [structure 1] | 8000 Hz | | |
| [structure 2] | 3070 Hz | 2900 Hz | |

In the above experiment, TATP and TNT were detected with 300 MHz resonators, while RDX was detected with 150 MHz resonators.

Example 6

Detection of Iohexole in Liquid Environment

The boronic acid derivative 10 synthesized for the detection of iohexole in, solution has the following structure:

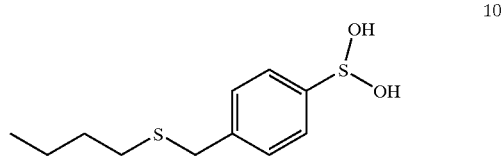

Iohexote is a compound used as a source for iodine needed for CT scans. However, the secretion of iohexole in the urine may also indicate certain gastro diseases.

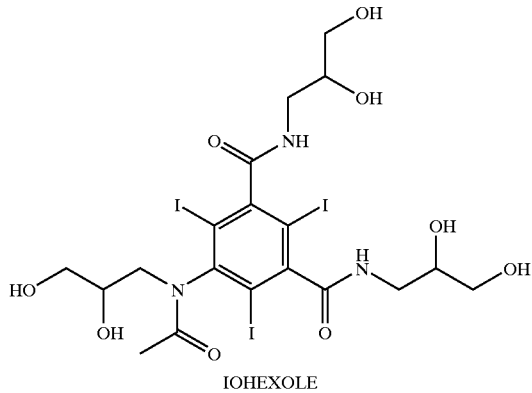

IOHEXOLE

The boronic acid derivative was prepared according to the following scheme:

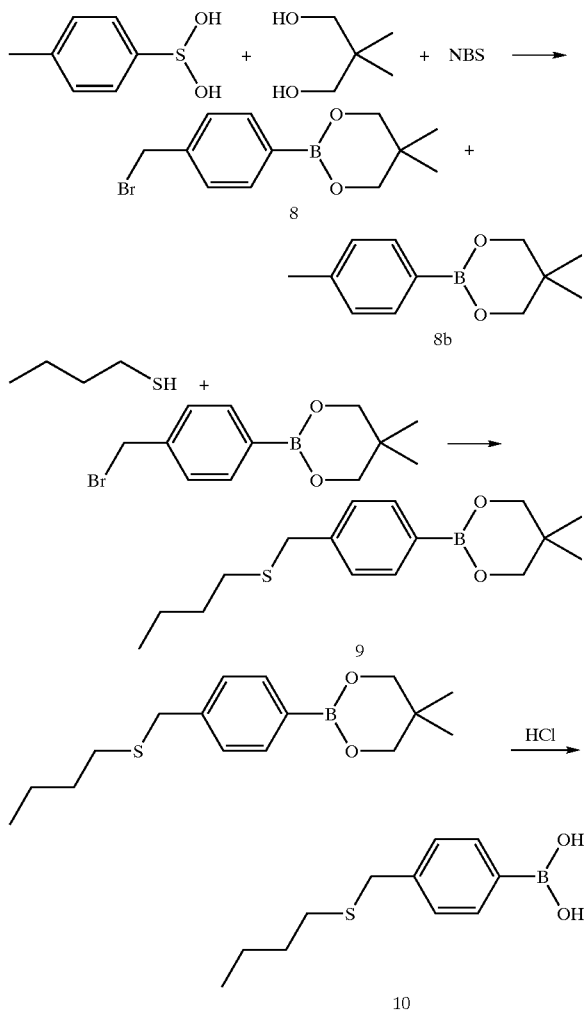

a) Synthesis of p-bromomethyl phenyl boronic acid-neopentyl ester (8)

p-Toluene boronic acid (750 mg.) and neopentyl glycol (600 mg.) were dissolved in 50 ml cyclohexane and heated at reflux for 1.5 hours. N-Bromosuccinimide (1.15 g.), benzoyl peroxide (25 mg.) and 150 ml cyclohexane were added and the solution was heated at reflux for additional 2 hours. The solution was cooled to room temperature, filtered and evaporated to give a mixture of 8 and 8a (total of 1.3 g, ~1:1 ratio), the yield of 8=47%.

NMR (CDCl$_3$, 250 MHz) δ=7.81+7.38 (Abq, 4H,Ar), 5.50 (s, 2H, ArCH$_2$Br), 3.77 (s, 4H, OCH$_2$C), 1.03 (s, 6H, C(CH$_3$)$_2$).

b) Synthesis of 9

Anhydrous potassium carbonate was added to a solution of 1-butanethiol (90 µl) in DMF. 8 (450 mg.) was added and the mixture was stirred over night The solution was dissolved in a mixture of hexane/ethyl acetate (1:3) and washed several times with water, dried over Na$_2$SO$_4$, filtered and evaporated to dryness. The product was purified by flash column chromatography (ethyl acetate-:dichloromethane 4:6 as eluent). Yield=15%.

NMR (CDCl$_3$, 250 MHz) δ=7.72+7.27 (Abq, 4H,Ar), 3.74 (s, 4H, OCH$_2$C), 3.68 (s,2H, ArCH$_2$S) 2.40 (m, 2H, SCH$_2$CH$_2$CH$_2$CH$_3$), 1.54 (m, 2H, SCH$_2$CH$_2$CH$_2$CH$_3$), 1.31 (m,2H, SCH$_2$CH$_2$CH$_3$CH$_3$), (m 1.00 (s, 6H, C(CH$_3$)$_2$), 0.85 (t, J=7 Hz, 3H, SCH$_2$CH$_2$CH$_2$CH$_3$).

c) Synthesis of 10

The boronic ester 9 (50 mg.) was hydrolyzed in THF/HCl 2N (1:1) over night at room temperature. The THF was evaporated, the residue was dissolved in ethyl acetate, washed with water and purified by three consequence chromatography columns ((i) CHCl$_3$:MeOH 97:3, (ii) CHCl$_3$:MeOH 99:1, n-Hexane:Ethyl acetate (gradient from 20% to 50% ethyl acetate)). Yield 15%.

NMR (CDCl$_3$, 250 MHz) δ=7.20+6.73 (Abq, 4H,Ar), 3.65 (s,2H, ArCH$_2$S) 2.43 (m, 2H, SCH$_2$CH$_2$CH$_2$CH$_3$), 1.28 (m, 4H, SCH$_2$CH$_2$CH$_2$CH$_3$), 0.88 (t, J=7 Hz, 3H, SCH$_2$CH$_2$CH$_2$CH$_3$).

Measurements were performed with 30 MHz resonators in water, The response of a resonator coated with the boronic acid derivative 10, in distilled water, was compared to that of a 25 µg/ml solution of iohexole as an analyte.

The response of the resonator to the iohexole solution was in the range of 600 Hz, Those skilled in the art will readily appreciate that various modification and changes can be applied to the embodiments of the invention as hereinbefore described and exemplified without departing from its scope defined in and by appended claims.

What is claimed is:

1. A piezoelectric crystal element for use in a sensor device for identifying at least one foreign material from environment, the crystal element comprising at least one crystal resonator in the form of an inverted mesa structure having a membrane-like region for electrodes to be located within said membrane-like region on opposite sides thereof, said membrane-like region being substantially thinner as compared to an end portion of the crystal resonator surrounding said membrane-like region, and having a certain resonance frequency value, a surface region of said at least one crystal resonator within said membrane-like region being modified by reactive molecules of a kind capable of interacting with said at least one foreign material to yield a reaction product that effects a change in the resonance frequency of said membrane-like region from said certain resonance frequency value, said change being indicative of the identity and quantity of said at least one foreign material.

2. The element according to claim 1, wherein said at least one crystal resonator is a quart crystal.

3. The element according to claim 1, wherein the electrodes are made of metal selected from Au, Pt and Al.

4. The element according to claim 3, wherein said electrodes are made of Au.

5. The element according to claim 3, wherein an Au-based glue is used for attaching the crystal element to a holder.

6. The element according to claim 1, and also comprising at least one additional crystal resonator which is in the form of an inverted mesa structure defining an additional membrane-like region, which is substantially thinner as compared to an end portion of the additional crystal resonator surrounding said additional membrane-like region and is characterized by a certain resonance frequency value, and which comprises additional electrodes located on opposite sides of said additional membrane-like region, said additional crystal resonator having a surface regions modified by reactive molecules of a kind capable of interacting with a foreign material of the environment to yield a reaction product that effects a change in the resonance frequency of the additional crystal resonator.

7. The element according to claim 6, wherein the surface regions of the at least two crystal resonators are modified with different reactive molecules, thereby enabling detection of various foreign materials contained in the environment.

8. A piezoelectric crystal element according to claim 1 wherein said surface region of said at least one crystal resonator is modified by a polymeric layer.

9. A piezoelectric crystal element according to claim 8 wherein said polymeric layer comprises at least one polymeric material selected from the group consisting of: polypyrrole, polythiophene, polytriphenylene, poly(dimethylamino)pyrrole, polyaniline, poly(N-phenyl)aniline, poly(N-methyl)aniline and polyfluoroaniline.

10. A piezoelectric sensor for use in a device for identifying at least one foreign material from environment, the sensor comprising a piezoelectric crystal element having at least one crystal resonator in the form of an inverted mesa structure having a sensing membrane-like region, which is substantially thinner as compared to an end portion of the crystal resonator surrounding said membrane-like region and has a certain resonance frequency value, and comprising electrodes formed on opposite sides of said at least one crystal resonator within said membrane-like region, said at least one crystal resonator having a surface region modified with molecules capable of interacting with at least one foreign material from the environment to which the crystal resonator is exposed to yield a reaction product that effects a change in the resonance frequency of said membrane-like region from said certain resonance frequency value, said change being indicative of the identity and quantity of said foreign material.

11. The sensor according to claim 10, wherein said at least one crystal resonator is a quartz crystal.

12. The sensor according to claim 10, wherein said electrodes are made of Au.

13. The sensor according to claim 10, wherein an Au-based glue is used for attaching the crystal element to a holder.

14. The sensor according to claim 10, and also comprising at least one additional crystal resonator which is in the form of an inverted mesa structure defining an additional membrane-like region, which is substantially thinner as compared to an end portion of the additional crystal resonator surrounding said additional membrane-like region and has a certain resonance frequency value, the additional crystal resonator comprising electrodes located on opposite sides of said additional membrane-like region, and having a surface regions modified by reactive molecules of a kind capable of interacting with a foreign material of the environment to yield a reaction product that effects a change in the resonance frequency of the additional crystal resonator.

15. The sensor according to claim 14, wherein the surface regions of different crystal resonators are modified with different reactive molecules, thereby enabling detection of various foreign materials contained in the environment.

16. A piezoelectric sensor device for identifying at least one foreign material from environment, the device comprising:
(a) a sensor including a piezoelectric crystal element having at least one piezoelectric crystal resonator in the form of an inverted mesa structure having a membrane-like region, which is substantially thinner as compared to an end portion of the crystal resonator surrounding said membrane-like region and has a certain resonance frequency value, and comprising electrodes located on opposite sides of said at least one crystal resonator within said membrane-like region, a surface region of said at least one crystal resonator within said membrane-like region being modified by reactive molecules of a kind capable of interacting with said at least one foreign material to yield a reaction product that effects a change in the resonance frequency of said membrane-like region from said certain resonance frequency value, said change being indicative of the identity and quantity of said at least one foreign material; and
(b) a control means operable for actuating said at least one crystal resonator, measuring the change in the resonance frequency of said membrane-like region, and generating measured data indicative of the identity and quantity of said at least one foreign material.

17. The device according to claim 16, wherein the control means comprises an actuator utility for operating said at least one crystal resonator, and a detector utility for detecting the frequency of the membrane-like region to enable the measurement of said change.

18. The device according to claim 16, wherein said at least one crystal resonator is a quartz crystal.

19. The device according to claim 16, wherein the electrodes are made of metal selected from Au, Pt and Al.

20. The device according to claim 19, wherein said electrodes are made of Au.

21. The device according to claim 19, wherein an Au-based glue is used for attaching the crystal element to a holder.

22. The device according to claim 16, wherein the piezoelectric crystal element comprises an array of spaced-apart crystal resonators, each resonator being in the form of the inverted mesa structure formed with a pair of electrodes at opposite sides of the membrane-like region thereof and having the modified surface region, thereby defining an array of sensing regions excitable by the environment to produce the changes in the frequencies of crystal resonators.

23. The device according to claim 22, wherein the surface regions of different crystal resonators are modified with different reactive molecules, thereby enabling detection of various foreign materials contained in the environment.

24. The device according to claim 22, wherein the crystal resonators are equally distanced from an actuator utility of the control means.

25. The device according to claim 24, wherein the crystal resonators are arranged in spaced-apart relationship along a circular path, the actuator utility being located on a central axis of the circle.

26. The device according to claim 22, wherein the piezoelectric crystal element comprises a disc formed with a circular array of the piezoelectric quartz crystal resonators, the control means comprising an actuator utility located in the center of the disc.

27. A piezoelectric sensor according to claim 16 wherein said surface region of said crystal resonator is modified by a polymeric layer.

28. A piezoelectric sensor according to claim 27 wherein said polymeric layer comprises at least one polymeric material selected from the group consisting of: polypyrrole, polythiophene, polytriphenylene, poly(dimethylamino) pyrrole, polyaniline, poly(N-phenyl)aniline, poly(N-methyl) aniline and polyfluoroaniline.

29. A piezoelectric sensor device for identifying at least one foreign material from environment, the sensor device comprising:

an array of spaced-apart crystal resonators, each crystal resonator being in the form of an inverted mesa structure having a membrane-like region, which is substantially thinner as compared to an end portion of the crystal resonator surrounding said membrane-like region and has a certain resonance frequency value, and having electrodes located at opposite sides of the crystal resonator within the membrane-like region, and a modified surface region, each of the crystal resonators being excitable by the environment to cause a change in the resonance frequency of the membrane-like region from said certain resonance frequency value; and an actuator utility for operating the crystal resonators, said actuator utility being equally spaced from each of the crystal resonators.

30. A piezoelectric crystal element for use in a sensor device for identifying at least one foreign material from environment, the crystal element comprising at least one crystal resonator in the form of an inverted mesa structure, which has a membrane-like region of a thickness of about several micrometers surrounded by a thicker end portion of the crystal resonator and having a certain resonance frequency value, and comprising electrodes located on opposite sides of said at least one crystal resonator within said membrane-like region, a surface region of said at least one crystal resonator being modified by reactive molecules of a kind capable of interacting with said at least one foreign material to yield a reaction product that effects a change in the resonance frequency of said membrane-like region from said certain resonance frequency value, said change being indicative of the identity and quantity of said at least one foreign material.

* * * * *